(12) United States Patent
Bayer et al.

(10) Patent No.: US 9,700,440 B2
(45) Date of Patent: *Jul. 11, 2017

(54) IMPLANT AND METHOD FOR MANUFACTURING SAME

(71) Applicant: BIOTRONIK VI Patent AG, Baar (CH)

(72) Inventors: Ullrich Bayer, Admannshagen-Bargeshagen (DE); Bodo Gerold, Zellingen (DE)

(73) Assignee: BIOTRONIK VI PATENT AG, Baar (CH)

( * ) Notice: Subject to any disclaimer, the term of this patent is extended or adjusted under 35 U.S.C. 154(b) by 614 days.

This patent is subject to a terminal disclaimer.

(21) Appl. No.: 13/937,097

(22) Filed: Jul. 8, 2013

(65) Prior Publication Data

US 2013/0304178 A1 Nov. 14, 2013

Related U.S. Application Data

(63) Continuation of application No. 12/836,068, filed on Jul. 14, 2010, now Pat. No. 8,512,483.

(Continued)

(51) Int. Cl.
*A61F 2/82* (2013.01)
*A61L 31/02* (2006.01)
(Continued)

(52) U.S. Cl.
CPC .............. *A61F 2/82* (2013.01); *A61L 31/022* (2013.01); *A61L 31/084* (2013.01);
(Continued)

(58) Field of Classification Search
CPC ............ C23C 8/68; C23C 8/70; C21D 8/0257
See application file for complete search history.

(56) References Cited

U.S. PATENT DOCUMENTS 4,520,511 A * 6/1985 Gianezio ............... A61F 2/3609
606/63
4,995,883 A 2/1991 Demane et al.
(Continued)

OTHER PUBLICATIONS

Lyakhovich, L. S., et al. "Anisotropy of the thermal expansion of a boride case on iron." Metal Science and Heat Treatment 13.7 (1972): 608-609.*

(Continued)

*Primary Examiner* — Jessee Roe
(74) *Attorney, Agent, or Firm* — Wagenknecht IP Law Group PC

(57) ABSTRACT

The present invention relates to a method for manufacturing an implant, in particular an intraluminal endoprosthesis, having a body containing metallic material, preferably iron. For controlling the degradation of the implant the method includes the following steps: (a) providing a first part of the implant body; and (b) performing heat treatment which alters the carbon content and/or the boron content and/or the nitrogen content in the structure of a near-surface boundary layer in the first part of the implant body in such a way that strain on the lattice or a lattice transformation, optionally following a subsequent mechanical load, is achieved in the near-surface boundary layer. Such an implant is also described.

22 Claims, 1 Drawing Sheet

Related U.S. Application Data

(60) Provisional application No. 61/246,173, filed on Sep. 28, 2009.

(51) Int. Cl.
| | | |
|---|---|---|
| *A61L 31/08* | (2006.01) | |
| *A61L 31/14* | (2006.01) | |
| *C23C 8/20* | (2006.01) | |
| *C23C 8/22* | (2006.01) | |
| *C23C 8/24* | (2006.01) | |
| *C23C 8/26* | (2006.01) | |
| *C23C 8/30* | (2006.01) | |
| *C23C 8/32* | (2006.01) | |

(52) U.S. Cl.
CPC ............... *A61L 31/148* (2013.01); *C23C 8/20* (2013.01); *C23C 8/22* (2013.01); *C23C 8/24* (2013.01); *C23C 8/26* (2013.01); *C23C 8/30* (2013.01); *C23C 8/32* (2013.01)

(56) References Cited

U.S. PATENT DOCUMENTS

| | | | |
|---|---|---|---|
| 5,383,928 A | 1/1995 | Scott et al. | |
| 5,888,201 A | 3/1999 | Stinson et al. | |
| 6,569,195 B2 | 5/2003 | Yang et al. | |
| 7,264,682 B2 * | 9/2007 | Chandran | C04B 35/62272 |
| | | | 148/210 |
| 8,512,483 B2 * | 8/2013 | Bayer | A61F 2/82 |
| | | | 148/206 |
| 2007/0141106 A1 | 6/2007 | Bonutti et al. | |
| 2007/0156231 A1 | 7/2007 | Weber | |
| 2007/0190231 A1 | 8/2007 | Chandrasekaran et al. | |
| 2007/0250155 A1 | 10/2007 | Simpson | |
| 2007/0282432 A1 | 12/2007 | Stinson et al. | |
| 2008/0152944 A1 | 6/2008 | Bonini et al. | |
| 2008/0281429 A1 | 11/2008 | Pawar et al. | |
| 2008/0312736 A1 | 12/2008 | Mueller et al. | |
| 2009/0187258 A1 | 7/2009 | Ip et al. | |
| 2009/0198320 A1 | 8/2009 | Mueller et al. | |
| 2013/0297006 A1 | 11/2013 | Bayer et al. | |

OTHER PUBLICATIONS

Metcalfe, Arthur G. "Interaction and fracture of titanium-boron composites." Journal of Composite Materials 1.4 (1967): 356-365.*
ASM International, Materials Park, Ohio, ASM Handbook vol. 1: Properties and Selection: Irons, Steels, and High-Performance Alloys, "Wrought Stainless Steels", pp. 841-846, Mar. 1990.*
Moravej, Maryam, and Diego Mantovani. "Biodegradable metals for cardiovascular stent application: interests and new opportunities." International journal of molecular sciences 12.7 (2011): 4250-4270.*
European Search Report for EP 10 17 5171.
ASM International, Materials Park, Ohio, Properties and Selection: Iron, Steels, and High-Performance Alloys, "Wrought Stainless Steels," vol. 1, pp. 841-846, Mar. 1990.
M. Tsujikawa, S. Noguchi, N. Yamauchi, N. Ueda, T. Sone, "Effect of molybdenum on hardness of low-temperature plasma carburized austenitic stainless steel," Surface & Coatings Technology, 201 2007) pp. 5102-5107.

* cited by examiner

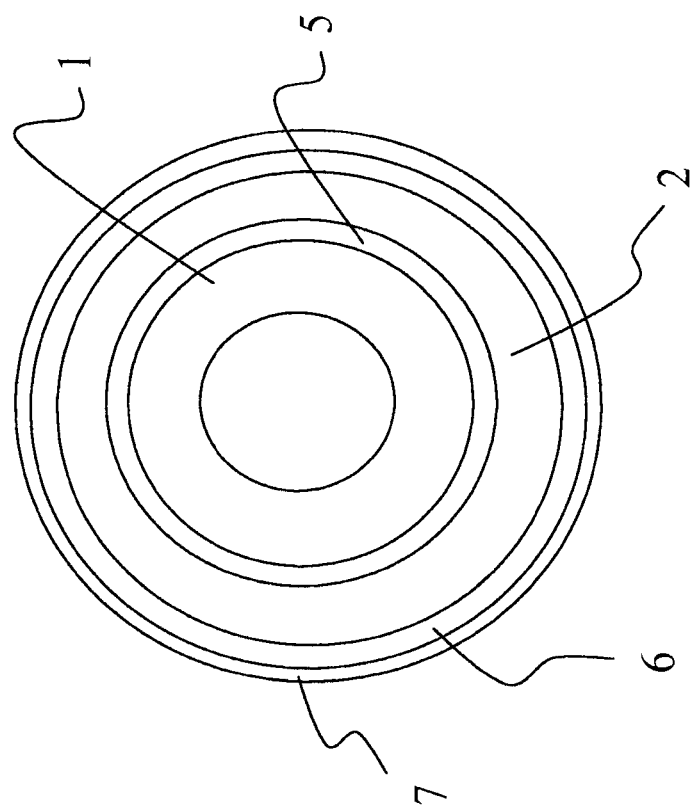

IMPLANT AND METHOD FOR MANUFACTURING SAME

CROSS REFERENCE TO RELATED APPLICATIONS

This application is a continuation of U.S. patent application Ser. No. 12/836,068, now U.S. Pat. No. 8,512,483, filed Jul. 14, 2010, which claims benefit of priority to U.S. provisional patent application Ser. No. US61/246,173, filed on Sep. 28, 2009; the contents of each are herein incorporated by reference in their entirety.

FIELD OF INVENTION

The present invention relates to a method for manufacturing an implant, in particular an intraluminal endoprosthesis, having a body containing metallic material, preferably iron, in particular an iron alloy, and a corresponding implant.

BACKGROUND OF THE INVENTION

A large variety of medical endoprostheses or implants for various applications are known from the prior art. Understood as implants within the meaning of the present invention are endovascular prostheses or other endoprostheses, for example stents, in particular wire mesh stents, attachment elements for bones, for example screws, plates, or pins, intramedullary pins, spiral bundle nails, Kirschner wires, wires for septal occluders, surgical suture material, intestinal clamps, vessel clips, prostheses for hard and soft tissue, and anchoring elements for electrodes, in particular for pacemakers or defibrillators.

Stents for the treatment of stenoses (vascular constrictions) are used particularly frequently as implants at the present time. Stents have a body in the form of an optionally perforated tubular or hollow cylindrical base lattice which is open at both longitudinal ends. The tubular base lattice of such an endoprosthesis is inserted into the vessel to be treated, and is used to support the vessel. Stents have become established in particular for the treatment of vascular diseases. Use of stents allows constricted regions in the blood vessels to be expanded, resulting in lumen gain. Although the optimal vessel cross section primarily necessary for successful treatment may be achieved by the use of stents or other implants, the permanent presence of such a foreign body initiates a cascade of microbiological processes which may lead to gradual overgrowth of the stent, and in the worst case may result in vascular occlusion. One approach to this problem is to fabricate the stent or other implants from a biodegradable material.

The term "biodegradation" refers to hydrolytic, enzymatic, and other metabolic degradation processes in the living organism which are primarily caused by the bodily fluids which come into contact with the biodegradable material of the implant, resulting in gradual disintegration of the structures of the implant containing the biodegradable material. As a to result of this process, at a certain point in time the implant loses its mechanical integrity. The term "biocorrosion" is frequently used synonymously for "biodegradation." The term "bioabsorption" includes the subsequent absorption of the degradation products by the living organism.

Suitable materials for the body of biodegradable implants may contain polymers or metals, for example. The body may be composed of several of these materials. The common feature of these materials is their biodegradability. Examples of suitable polymeric compounds include polymers from the group including cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyortho esters, polyethylene terephtalate (PET), polymalonic acid (PML), polyanhydrides, polyphosphazenes, polyamino acids, and the copolymers thereof, as well as hyaluronic acid. Depending on the desired characteristics, the polymers may be present in pure form, derivatized form, in the form of blends, or as copolymers. Metallic biodegradable materials are primarily based on alloys of magnesium and iron. The present invention preferably relates to implants whose biodegradable material contains, at least in part, a metal, preferably iron, manganese, zinc, and/or tungsten, in particular an iron-based alloy (referred to below as "iron alloy" for short).

In the implementation of biodegradable implants, the aim is to control the degradability corresponding to the intended treatment or use of the particular implant (coronary, intracranial, renal, etc.). For many therapeutic applications, for example, it is an important target corridor for the implant to lose its integrity over a period of four weeks to six months. In this regard "integrity," i.e., mechanical integrity, refers to the characteristic that the implant does not undergo hardly any mechanical losses compared to the undegraded implant. This means that the implant is still mechanically stable enough to ensure that, for example, the collapse pressure drops only slightly, i.e., to a maximum of 80% of the nominal value. Thus, when integrity is present the implant is still able to fulfill its primary function of keeping the blood vessel open. Alternatively, integrity may be defined such that the implant is mechanically stable enough that in a load state in the blood vessel it to undergoes minimal changes in its geometry, for example does not show appreciable collapse, i.e., under a load of at least 80% of the dilation diameter, or, in the case of a stent, has very little fracturing of supporting struts.

Implants containing an iron alloy, in particular iron-containing stents, are particularly economical and easy to manufacture. For the treatment of stenoses, for example, these implants do not lose their mechanical integrity or support effect until after a comparatively long time, i.e., after a residence time of approximately two years in the treated organism. This means that for implants containing iron, the collapse pressure decreases too slowly over time for this application.

A long residence time of implants may also lead to complications if, as a result of its ferromagnetic properties, the implant undergoing disintegration does not permit examination of the treated patient using magnetic resonance tomography. Furthermore, for orthopedic implants (bone plates, for example), the formation of new bone substance may result in mechanical stresses between the implant which is degrading too slowly and the bone substance. This produces bone deformations or malformations, especially in children and adolescents. For such applications, therefore, it is desirable to be able to expand the potential of use in particular of iron-based implants through more rapid degradation.

Various mechanisms for controlling the degradation of implants have been described in the prior art. These mechanisms are based, for example, on inorganic and organic protective layers or a combination thereof which resist the human corrosive environment and the corrosion processes occurring therein. Previously known approaches are characterized by the achievement of barrier layer effects which are based on spatially separating, with as few defects as possible, the corrosion medium and a metallic material. As a result, the degradation time is increased. This ensures degradation protection by use of protective layers of various compositions and by defined geometric distances (diffusion barriers) between the corrosion medium and the magnesium base material. Other approaches are based on alloy components of the biodegradable material of the implant body which influence the corrosion process by shifting the position in the electromotive series. Further approaches in the area of controlled degradation produce predetermined breaking effects to by applying physical changes (for example, localized changes in cross section) in the stent surface (for example, local multilayers of chemically different compositions). However, the previously described approaches are usually not able to place the disintegration occurring due to the degradation process and the resulting strut fractures in the required time window. The result is degradation of the implant which begins either too early or too is late, i.e., which has excessive variability.

Implants are known from documents EP 923 389 B1 (WO 99/03515 A2) or WO 2007/124230 A1 which are degradable in vivo as the result of corrosion. The material of the known implants contains iron as the primary component, as well as carbon in a specific, predetermined concentration. The disadvantage of these alloys is that the pure binary system composed of carbon and iron experiences a great loss in ductility with increasing carbon content, without a corresponding decrease in corrosion resistance.

In EP 08172105.2 various iron alloys, for example an alloy system based on Fe and Mn, are described which, although they are slightly more susceptible to corrosion compared to pure iron in an artificial medium which duplicates physiological conditions, they consistently degrade too slowly. A further disadvantage is that Mn stabilizes the cubic face-centered austenitic phase of the iron. This results in a mixed structure of austenitic and cubic body-centered ferritic phases, depending on the content of additional alloy elements and the preceding heat treatment, as well as the specific content of Mn itself. The particular percentage of these phases may fluctuate greatly from charge to charge on account of these numerous influencing variables. The resulting variations in hardening behavior of cut stents makes dimensioning, which is based on the assumption of specific strength and elongation values, difficult or impossible.

SUMMARY OF THE INVENTION

Consequently, the feature of the present invention is to provide a method for manufacturing an implant which causes degradation of the implant in the desired target corridor, in particular for implants containing an alloy based on iron, in a rather short period of time without a loss in ductility. The aim is for the degradation to occur at a controllable point in time, and to allow even implants with complex shapes to be provided with the desired degradation characteristics. Correspondingly, a further object of the invention is to provide such an implant.

The above feature is achieved by use of a method including the following steps: (a) providing a first part of the implant body; and (b) performing heat treatment which alters the carbon content and/or the boron content and/or the nitrogen content in the structure of a near-surface boundary layer in the first part of the implant body in such a way that strain on the lattice or a lattice transformation, optionally following a subsequent mechanical load, is achieved in the near-surface boundary layer.

DESCRIPTION OF THE DRAWINGS

The FIGURE schematically shows a cross section of a stent body manufactured according to the method described in Example 6. The stent body is composed of two tubes situated one inside the other, namely, a first inner tube 1 and a second outer tube 2. The first tube 1 is made of C15 steel, and the second tube 2 is made of a C10, C15, or C20 steel. A carburized connecting zone 5 is present in the boundary region between the first tube 1 and the second tube 2. In addition, a carburized border zone 6 is provided in an outer boundary region of the second tube 2. By means of the above-described tribochemical treatment an additional boundary zone 7 situated farther outward than region 6 is provided in which the material has been tribochemically treated using chloride ions. This zone 7 is omitted if the tribochemical treatment has not been performed. The layer thicknesses shown in the FIGURE are not to scale

DETAILED DESCRIPTION OF THE INVENTION

In the present invention the body of the implant includes at least a part of the implant, preferably the main part of the implant, which provides for mechanical integrity of the implant. The first part of the implant body may be a portion of this main part of the implant, or may include the entire main part of the implant. Thus, the above wording does not exclude a one-piece implant body. This variant is expressly encompassed by the special case in the present invention that only a single first part of the implant body exists.

The term "structure" hereinafter refers to the configuration of the components of solids (solid bodies), in particular the configuration of crystallites (grains), pores, amorphous regions, and grain boundary regions of the implant body. In addition, the term "near-surface structure" refers to the volumetric region of the structure of the corresponding part of the implant body which extends from the surface to a given (small) depth of the implant body. This volumetric region extending from the surface to a given (small) depth is also referred to as "near-surface boundary layer," or "boundary layer" for short.

The advantage of the method according to the invention is that, by means of a very simple and economical process, the structural properties in a boundary layer, i.e., in a near-surface region, are altered in such a way that under further mechanical load, cracks form in the near-surface boundary layer which accelerate the degradation in the treated part of the implant body. The degradation time period achieved by the method according to the invention is in the range of 3 to 9 months. In particular, the degradation time may be reduced to a maximum of 75%, preferably to a maximum of 60%, compared to the degradation time of an implant manufactured without heat treatment.

A further advantage of the approach according to the invention is that optimal mechanical properties of the implant, in particular adequate ductility, in the volumetric portion of the implant not included in the boundary layer are maintained through the selection of the substrate material. Only a (very small) volumetric portion located near the surface is produced which has degradation characteristics that are different from the base material. These degradation characteristics result from the internal stresses in the boundary layer caused by lattice strain or the altered lattice structure in the boundary layer due to the change in composition. The change in the lattice structure may be induced as the result of a mechanical load, in particular during dilation of the implant, leading to cracks. These internal stresses also produce cracks under mechanical load on regions having lattice strain. Thus, the invention realizes a particularly advantageous combination of volume and boundary region characteristics. In addition, a gradient in the corresponding altered to composition is produced in the boundary region.

In one exemplary embodiment of the present invention, after step (b) a second part of the implant body is provided, after which the second part of the implant body is positioned over the first part in such a way that the second part adjoins the first part of the implant body, at least in a partial region of the near-surface boundary layer, and the system composed of the first and second parts of the implant body is then subjected to heat treatment according to step (b).

In this exemplary embodiment a multilayer composite is produced in which the first part and the second part of the implant body form regions which differ in composition, in particular with regard to the carbon, boron, and nitrogen content. Over the cross section of the implant body, regions having the initial composition of the implant body alternate with (boundary) regions having a different composition with regard to the carbon, boron, and nitrogen content. The heat treatment after positioning the second part causes the boundary layer formed by the heat treatment for the first part to form a connecting layer (interface) between the first and the second part, and as the result of diffusion processes the second part is affixed to the first part of the implant body. Such a sandwich structure has an advantageous combination of degradation characteristics and mechanical properties.

It should be noted at this point that formation of a sandwich structure described above is not essential for the effectiveness of the present invention. The embodiment described above merely represents one advantageous variant of the invention. The invention may be realized on the one hand by the fact that the implant body is composed only of a (single) first part, and on the other hand by the fact that the implant body is composed of a first part and a plurality of second parts, wherein step (b) is advantageously repeated after each positioning of an additional second part over the underlying parts of the implant body. Thus, it is conceivable that, for example, between 5 and 20 composite layers may be provided over an implant cross section of 100 µm.

Several possibilities are described below for achieving lattice strain or lattice transformation in the near-surface boundary layer by means of heat treatment. In principle, heat treatment according to the invention may be used to: (I) evoke the enrichment of Fe compounds in the boundary layer and lattice strain thus produced; or (II) destabilize, for example, the austenitic phase which is stabilized in the initial composition in such a way that the austenitic phase is converted to the harder, more crack-prone martensitic lattice as the result of subsequent mechanical load.

Variant I is achieved by using the approaches described in sections 1 through 3 below. This variant has the further advantage that the Fe compounds are able to form local elements which additionally accelerate the degradation.

Variant II is achieved using the approach described in section 4. In this variant the austenitic lattice becomes metastable as a result of the heat treatment, and converts to the martensitic structural form.

Which of the two variants I or II may be used depends on the particular initial composition of the implant bodies. Variant I is used for Fe compounds in which the austenitic phase is not stabilized (for example, for a low Mn content and/or a low C content). Variant II is used for initial compositions in which the austenitic phase is first stabilized, i.e., in which the compositions have a high Mn and/or C content.

Both variants I and II share the common feature that the elements resulting from the heat treatment diffuse into the interior of the implant body before they form compounds with Fe, or before they must diffuse outwardly from the interior. Due to thermodynamic constraints this diffusion must come to a standstill, since the lattice is saturated with the interstitial atoms, and Fe compounds form, i.e., the lattice converts, when the solubility limit is exceeded. Consequently, when the supply of the element or the treatment time as well as the corresponding temperature selection are limited, the thickness of the near-surface boundary layer in which the structural change occurs remains limited.

1. Carburization

In one preferred exemplary embodiment of the method according to the invention, during the heat treatment according to step (b) the carbon content in the structure of the near-surface boundary layer is increased by carburization, the boundary layer preferably having a maximum thickness of approximately 20 µm, particularly preferably approximately 10 µm.

Internal stresses arise in such a near-surface zone which is enriched with carbon and carbon compounds, in particular when grades of steel such as C10, C15, or C20 are used. In this regard the carbon content and the extent of the boundary layer are selected such that the total maximum carbon content of the implant does not exceed 0.45% by weight, so that the mechanical properties of the implant, in particular the ductility resulting from the changes near the surface, are not impaired.

When the implant is dilated, the internal tensile stresses arising in the boundary layer of the implant body favor the formation of cracks in the surface, which in turn facilitate the degradation. Furthermore, the pulsing stresses which are always present also cause degradation based on stress corrosion cracking during continued use of the implant. However, the cracks which propagate in the substrate of the implant do not result in failure of the entire implant (for a stent, for example, a strut fracture), since the cracks are arrested by the less crack-susceptible, tough matrix of the base material which contains less carbon. As a result, the corrosion has the character of surface corrosion.

In a further preferred exemplary embodiment, the average carbon concentration in the near-surface boundary layer after carburization is 0.5% by weight to 2% by weight, particularly preferably 0.8% by weight to 1.3% by weight.

The required mechanical properties of the implant, for example $Rp_{0.2}$ of at least 300 MPa and $A_5$ of at least 15%, are achieved in particular in the treated part of the implant body in the stated range of the carbon content. The parameter $Rp_{0.2}$ represents the yield strength, which identifies a given material-dependent stress (in this case: 300 MPa) which results in a plastic deformation of 0.2%. The so-called 0.2% yield strength is also referred to as the "technical elastic limit." The parameter $A_5$ refers to a material variable which represents the remaining elongation of the sample after break, relative to the initial measured length. This value characterizes the deformability of the material. The parameter $A_5$ is calculated from the ratio (in percent) of the remaining elongation of a sample in the tensile test relative to its initial measured length.

In this exemplary embodiment of the present invention, the carbon concentration is set so that the composition of the structure is in the perlite region of the iron-carbon diagram. Since perlite represents a phase mixture of cementite and ferrite, the cementite acts as a cathodic region of a local element. The corrosion of the adjacent ferrite is thus accelerated. The more corrosion-resistant cementite lamellae ($Fe_3C$) remain insular for a period of time, so that the surface is fissured by selective corrosion.

It is also advantageous when the implant body is cooled after the carburization in such a way that additional internal stresses arise in the near-surface boundary layer. During dilation these internal stresses likewise produce cracks in the surface which may act as a starting point for the degradation.

In a further exemplary embodiment, the body of the implant has a maximum cementite content of approximately 40% by weight in the boundary layer resulting from the heat treatment.

2. Boronization

In a further advantageous exemplary embodiment, during the heat treatment according to step (b) the boron content in the structure of the near-surface boundary layer is increased by boronization, the boundary layer preferably having a thickness of approximately 5 µm to approximately 300 µm. The layer thickness is dependent, among other factors, on the carbon content of the initial composition of the corresponding part of the implant body.

As the result of boronization, a boride layer is formed on the surface which contains FeB and $Fe_2B$ in the case for which iron is the predominant material of the implant body. These boron compounds grow into the structure in a tooth- or stem-like manner, perpendicular to the surface of the implant body, and are well anchored in the structure. The boron compounds result in an approximately 25% volume increase in the treated border zone. In particular for loads in alkaline media, such a boundary layer results in decreased corrosion is resistance for favorable mechanical properties. In particular, the aim is to obtain a monophase boundary layer composed of $Fe_2B$ as a function of the initial composition of the implant body, i.e., as a function of the Fe content thereof. The hardness that is achievable with such a boundary layer is approximately 2100 HV for a monophase layer of FeB, and approximately 2000 HV for a layer of $Fe_2B$. The boron content in FeB is 16.23% by weight, and in $Fe_2B$ is 8.83%. For a lower Fe content in the initial composition, the boronization produces a greater proportion of regions which do not contain $Fe_2B$.

During boronization, elements such as silicon and carbon are also forced beneath the boride layer, whereby a nonaustenitizable ferritic layer may form which as a local element is likewise able to accelerate the corrosion. In the case of locally increased manganese contents, islands of retained austenite may be produced in the ferritic surface matrix. In contrast, most metallic alloy elements are soluble in the boride layer. This applies in particular to manganese, whose proportion in the boride layer essentially corresponds to that of the base material, and chromium, for which slightly higher proportions are found in the boride layer. Therefore, the composition of the boride layer would actually have to be characterized as (Fe, M)B or (Fe, M)$_2$B, where M represents one or more elements which are soluble in the layer.

In one particularly preferred exemplary embodiment, the average concentration of boron in the near-surface boundary layer after the boronization is 1% by weight to 20% by weight, preferably 7% by weight to 10% by weight.

The implants are preferably boronized over a period of approximately 15 minutes to approximately 6 hours. The boronization preferably takes place in a temperature range between approximately 850° C. and 1000° C. The process parameters for the boronization, in particular the temperature and the boronization period, influence the bonding strength and corrodibility of the near-surface boundary layer (boronization zone). At elevated temperatures, longer and less uniform tooth- or stem-like structures form which grow from the surface into the solid body as described above. In this case the corrodibility of the implant is further increased, since after the stem structures dissolve out of the matrix a very fissured surface remains which is able to undergo further improved degradation due to its large surface area. At lower temperatures and shorter boronization times the tooth- or stem-like structures are more uniform and smaller. It has been shown that the use of higher temperatures and correspondingly shorter process times is more favorable overall, since the diffusion depth of the boron remains limited for shorter process times, and the entire implant cross section is not boronized. Boronization of the entire cross section would result in excessive overall embrittlement of the implant, so that continuous fractures in the implant, for example strut fractures for stents, could arise during dilation.

3. Nitriding and Nitrocarburization

In a further exemplary embodiment, during the heat treatment according to step (b) the nitrogen content in the structure of the near-surface boundary layer is increased by nitriding, or the carbon and nitrogen content in the structure of the near-surface boundary layer is increased by nitrocarburization, the boundary layer preferably having a maximum thickness of 150 µm. The particular advantage of such a procedure is that the implants treated in this manner are dimensionally stable and have high dimensional accuracy, since no structural transformation occurs during nitriding.

Nitriding or nitrocarburization produces nitrides, in particular the $\gamma'$-nitride, or more preferably, the $\epsilon$-carbonitride, which likewise form adjacent zones (local elements) which differ from the surrounding regions with respect to their position in the electromotive series and their brittleness. In this manner anodic and cathodic subregions are formed and strain is produced. The surroundings of the nitrides therefore corrode more rapidly. This results in intensified fissuring of the surface, which facilitates further accelerated corrosion.

Preferred nitriding processes in the present patent application are salt bath nitriding, gas nitriding (for example, in ammonia at a temperature of 500° C. to 530° C.; NHD approximately 0.1 mm to 0.9 mm), and plasma nitriding in a temperature range of 420° C. to 520° C. "NHD" refers to the nitriding hardness depth, which characterizes the distance to the surface (in the cross section) in a sample for which the value of the microhardness, at 50 HV, is still usually 0.5 higher than the base material hardness. An advantage of salt bath nitriding is that the implant may be partially nitrided, whereby the nitrided region is specified by immersing the implant in the salt bath. For simple partial nitriding in plasma, portions of the implant may be mechanically covered, for example by using a clamping device. After nitriding, the implant preferably has a concentration of 0.5% by weight to 17% by weight, preferably 5% by weight to 12% by weight, of nitrogen in the near-surface boundary layer.

Nitrocarburization may be carried out, for example, in a temperature range of 570° C. to 580° C., preferably in a gas mixture which is able to release nitrogen (ammonia, for example) and carbon (carbon dioxide, methane, ethane, propane, for example).

In one particularly preferred exemplary embodiment, the average concentration in the near-surface boundary layer after nitrocarburization is 0.5% by weight to 7% by weight, preferably 0.5% by weight to 4% by weight, particularly preferably 0.5% by weight to 2% by weight carbon, and 0.5% by weight to 17% by weight, preferably 5% by weight to 12% by weight nitrogen. It is noted that nitrides have a given solubility for carbon. Thus, the γ'-nitride may incorporate up to 0.2% by weight carbon, and the ε-nitride, as much as 4% by weight. By regulating the nitriding potential or nitriding parameter N the growth and the composition of the nitriding layer may be influenced in a targeted manner. In the γ' phase the stoichiometric composition fluctuates only slightly. For example, the proportion of nitrogen in percent by weight may vary between approximately 5.7 and approximately 6.1% N. In contrast, the ε phase may contain between approximately 5.6 and approximately 11% N, for example.

Nitrided or nitrocarburized layers are generally composed of two zones, an interior zone (inner zone) and an exterior zone which forms the surface of the implant in the treated region. Both zones form the near-surface boundary layer, the N and optionally also the C content of which is modified by nitriding or nitrocarburization according to the invention.

The inner zone, which represents the diffusion layer, may be characterized by the formation of nitride needles. The thickness of the diffusion layer depends on various parameters (with regard to the material of the implant body, in particular the alloy components, as well as the temperature, the nitriding or nitrocarburization time, and the is gas composition for gas nitriding or gas nitrocarburization, which in particular may be expressed by the nitriding parameter N (proportion of ammonia in the gas mixture).

The outer nonmetallic zone, which is approximately 5 μm to approximately 30 μm thick, is essentially composed of γ'-nitrides ($Fe_4N$), ε-nitrides ($Fe_2 \ldots 3N$), and optionally carbonitrides ($Fe_xC_yN_z$). Alloyed steels contain the alloy elements in addition to nitrides and carbonitrides. The outermost region of the exterior layer, oriented in the direction of the surface of the implant, may be provided as pore space.

As a whole, in the method according to the invention it is advantageous for the desired characteristic profile of the implant to be easily adjustable by means of the process parameters of process temperature, partial pressure, composition of the process gas, and process time. This applies in particular to the degradation rate, as well as to the wear resistance of the implant to abrasion.

A further advantage of the method according to the invention is that pores are formed in the implant in the region of the near-surface boundary layer by means of the heat treatment used according to the invention. These pores may be used as a vehicle for transport of pharmaceutically active substances, and also for simplifying the anchoring of the implant in the surrounding tissue, for example in bone.

A further advantage of the near-surface boundary layer produced using the method according to the invention is that the layer provides increased resistance of the implant to abrasive wear or to the frictional component of fretting corrosion. In particular for applications which necessarily involve friction of the implant with itself, with another implant, or with a hard tissue (bone), for example for screwing in a bone screw, this characteristic of the implant manufactured by the method according to the invention is advantageous.

4. Decarburization

In a further embodiment of the present invention, during the heat treatment according to step (b) the content of carbon in the structure of the near-surface boundary layer of the implant is reduced by decarburization, the boundary layer preferably having a maximum thickness of approximately 50 μm.

This approach according to the invention is used in particular for implants having a composition of manganese- and carbon-alloyed iron-based material such that the austenitic phase is stabilized. For example, the material of the implant body may contain an iron-based alloy having 0.7% by weight carbon and 12% by weight manganese. Heat treatment in an oxidizing atmosphere (in pure oxygen or air, for example) burns off the carbon in the near-surface boundary layer of the implant. This reduces the carbon content in the boundary layer by only 0.1% by weight at a depth of 5 μm. Depending on the process control, this surface decarburization may extend to a depth of 50 μm. At that location the carbon content is then approximately 0.06% by weight. Averaged over the entire boundary layer, the carbon content is 0.1% by weight to 0.3% by weight, preferably 0.15% by weight to 0.25% by weight.

When an implant treated in this manner is subsequently subjected to plastic deformation, for example during dilation, the mechanical deformation of the near-surface boundary layer is greater than in the regions within the implant. In the near-surface boundary region which contains less carbon, due to the decreased carbon content the austenitic structure is metastable, resulting in a stress-induced martensite. This martensite is characterized by greater mechanical strength and a lower elongation at break. During dilation and also under further mechanical load after dilation, for example as the result of motion of a vessel, the stress-induced martensite has a tendency toward crack formation. Upon contact with bodily fluid, zones arise within the cracks in which chloride ions present in the bodily fluid are more strongly adsorbed. The passivity in the crevice is eliminated as a result of the reduced mass transfer. The corrosion products which form during crevice corrosion hydrolyze, and the localized pH drops. This further accelerates the corrosion, which thus increasingly attacks regions which are also at a remote distance from the crack.

The above-described corrosion processes are facilitated by mechanical loads on the implant. For a stent, such mechanical load is provided by the pulsing stress on the stent as the result of vascular contraction. For orthopedic implants, mechanical load may be produced by the alternating tensile-compressive load caused by the cardiac rate (for a filigreed bone screw or a distal fibular tibia plate for small children, for example). This mechanical load promotes stress corrosion cracking. Supercritical cracks, which in the worst case would result in sudden failure of the implant, are prevented by the fact that a tough austenitic region insensitive to cracking is present beneath the near-surface boundary layer, i.e., inside the implant, which accumulates and in some cases also dissipates the cracking energy in the cubic face-centered austenitic lattice. However, the cracks which are arrested in this region cause new crevice corrosion, and the corrosion process similarly continues in an accelerated manner up until the desired self-disintegration of the implant.

In one particularly preferred exemplary embodiment, the average concentration of carbon in the near-surface boundary layer after decarburization is approximately 0.1% by weight to approximately 0.3% by weight. The manganese content is preferably approximately 10% by weight to approximately 19.5% by weight.

The degradation may be further accelerated by quickly cooling the part of the implant body treated by decarburization. This means that this part of the implant body is quenched by use of a preferably liquid cooling medium (besides air). The quick cooling causes a rapid structural transformation, resulting in hardness cracks due to the different coefficients of thermal expansion of the austenite and the martensite. These cracks likewise form a point of attack for the above-described corrosion. For example, the implant may be quenched in ice water/salt solution at a temperature of −10° C., or in liquid nitrogen at a temperature of −196° C., starting from the austenization temperature.

5. Additional Coating and Tribochemical Treatment

It is also advantageous, after the heat treatment according to step (b), to coat the implant body on at least a portion of its surface with a pharmaceutically active substance, in particular embedded in a polymer, for example a polylactide, a polyglycoside, or a copolymer of same, particularly preferably PLLA or PLGA, or a blend of the referenced polymers. This additional coating may be used for implants which have been manufactured according to either variant I or variant II of the heat treatment.

The term "pharmaceutically active substance" (or therapeutically active substance, active ingredient) within the meaning of the invention refers to a plant, animal, or synthetic active substance (medicament) or a hormone which in appropriate dosages is used as a therapeutic agent for influencing states or functions of the body, as a substitute for active substances such as insulin which are naturally produced by the human or animal body, and for eliminating or rendering harmless pathogenic agents, tumors, cancer cells, or substances foreign to the body. The release of the substance into the environment of the implant has a positive effect on the healing process, or counteracts pathological changes in the tissue resulting from surgical procedures, or in the field of oncology is used to render malignant cells harmless.

These types of pharmaceutically active substances have an anti-inflammatory and/or antiproliferative and/or spasmolytic effect, for example, by means of which restenosis, inflammation, or (vascular) spasms, for example, may be avoided. Such substances may be composed, for example, of one or more substances from the active substance group of calcium channel blockers, lipid regulators (fibrates, for example), immunosuppressants, calcineurin inhibitors (tacrolimus, for example), antiphlogistic agents (cortisone or dichlofenac, for example), anti-inflammatory agents (imidazole, for example), antiallergic agents, oligonucleotides (dODN, for example), estrogens (genistein, for example), endothelium-forming agents (fibrin, for example), steroids, proteins, hormones, insulins, cytostatic agents, peptides, vasodilators (sartane, for example), and substances with antiproliferative activity, taxole or taxane, in the present case preferably paclitaxel or sirolimus.

A coating with a polymer, for example a polylactide, a polyglycoside, or a copolymer of same, particularly preferably PLLA or PLGA, or a blend of the referenced polymers, which contains the pharmaceutically active substance is particularly advantageous, since the reduction in pH in the region of the implant surface caused by the degradation of the polymer represents an additional acceleration factor for the corrosion, especially for an implant containing an iron alloy.

Alternatively or additionally (after the heat treatment and before coating of the implant body with a pharmaceutically active substance), in a further exemplary embodiment the implant body may be tribochemically treated with blast particles on at least a portion of its surface.

In the present patent application, the term "tribochemical treatment" refers to a mechanical and optionally chemical surface treatment by bombardment or irradiation of the treated portion of the body surface by use of blast particles. The method is also referred to as particle blasting. The blast particles are particles composed of one or more materials having an average particle size in the nano- or micrometer range. The particle size is determined using a scanning electron microscope (for particle sizes less than or equal to 3 μm) or a light optical microscope (for particle sizes greater than 3 μm). The electromicrographs or light optical micrographs are measured, and the average particle size is determined from the measured values by averaging (arithmetic mean), for example. Thus, the blast particles consist not of individual atoms, ions, or compounds, but, rather, a group or structure of atoms, ions, or molecular compounds. Tribochemical treatment is generally carried out at room temperature, i.e., in the cold state. In the following description, reference is made primarily to irradiation using blast particles as a tribochemical treatment method.

By use of blast particles, tribochemical treatment of at least a portion of the body surface produces additional surface roughness and/or a coating on the treated part of the body surface in a particularly simple and economical manner. The surface formed by the heat treatment is thus modified in a targeted manner with respect to its chemical composition, degree of solidification, and/or surface morphology in such a way that a change in the degradation characteristic of the treated implant is also achieved. The surface modifications resulting from the tribochemical treatment depend in particular on the nature, size, shape, and chemical composition of the blast particles, the blast pressure, and the distance between the blast nozzle and the implant body, as well as the material of the implant body.

Used in particular for the tribochemical treatment are blast particles containing at least one salt, preferably a compound from the group containing NaCl, CaCl, and $MgCl_2$, in particular dry $MgCl_2$.

The blast particles containing at least one salt are blasted onto the surface of the implant at a specified, predetermined pressure. The pressure range from 0.5 to 5.0 bar is advantageous. The treatment period is in a range from 0.5 to 30 minutes. Application of pressure during the irradiation causes not only roughening of the body surface, but also partial adherence of the blasted salts and optionally additional blast particles to the body surface. The blast particles containing the corrosive salts may also be mixed with blast particles composed of inert hard material, preferably a compound from the group containing oxides, in particular $Al_2O_3$, $SiO_2$, $ZrO_2$, and MgO, and carbides, in particular TiC, SiC, $B_4C$, B—BN, beryllium carbide, and oxycarbides, nitrides, in particular TiN, cubic boron nitride (c-BN, β-BN, "Borazon"), $Si_3N_4$, AlN, and TiAlN, carbonitride, natural or synthetic diamond, and boron. The salts which adhere to the surface of the implant body cause accelerated corrosion of the surface.

In this exemplary embodiment it is also possible to exclusively use corrosive salts as blast particles. In particular, dry $MgCl_2$ in the form of a granular salt of defined grain size is used as a blast medium without the addition of further abrasive hard materials. For this reason dry $MgCl_2$ should be used, since otherwise there is a risk of agglomeration of the material due to severe hygroscopy.

Due to their low hardness, $MgCl_2$ particles cause no significant mechanical surface alteration, i.e., no significant surface roughening. However, a large portion of the $MgCl_2$ particles adhere to the surface of the implant. Corrosion of the surface is initially delayed by storing the implant treated in this manner under an extremely dry atmosphere with the exclusion of air. The adherent $MgCl_2$ does not begin to exert a strongly corrosive effect until implantation and contact of the implant, for example a stent, with bodily fluid, resulting in accelerated degradation.

When storage has not been performed under exclusively dry conditions, until they disintegrate in the tribochemically produced submicro-roughening the $MgCl_2$ particles temporarily accelerate corrosion in the presence of humidity, thus enlarging the dimensions of the cavity of the submicro-roughening.

In a further preferred exemplary embodiment, after tribochemical treatment the tribochemically treated implant body is aged under increased humidity, in particular at relative humidity higher than 80%, and/or at elevated temperature, in particular at a temperature greater than 50° C.

Notable accelerated corrosion of the body surface is achieved by the referenced aftertreatment of the implant body, in particular after tribochemical treatment by bombardment with blast particles containing at least one salt. This aftertreatment, in particular aging under increased humidity, produces very specific, localized pitting corrosion effects which are qualitatively different.

In summary, the surface structure resulting from the tribochemical treatment may be characterized by the following morphometric and chemical properties: micro-roughening in the roughness range Rz of several μm; submicro-roughening (caverns) in the roughness range Rz of <1 μm; chemical modification as the result of adhered conductive blast particles and/or salts; and a dislocation density, increased in comparison to the base material, to a depth of the implant body volume of up to approximately 5 μm, starting at the body surface. This surface structure results in further acceleration of degradation of the implant.

6. Implant

The object stated above is further achieved by use of an implant which is obtainable using a method according to the invention described above. Such an implant has the advantages stated above in conjunction with the manufacturing method according to the invention.

The object stated above is further achieved by use of an implant, whereby in at least a portion of the implant body the following are present in the structure of the near-surface boundary layer in comparison to the respective concentration in the remaining structure: an increased carbon content, preferably in a concentration of 0.5% by weight to 2% by weight, particularly preferably in a concentration of 0.8% by weight to 1.3% by weight; an increased boron content, preferably in a concentration of 1% by weight to 20% by weight, particularly preferably in a concentration of 7% by weight to 10% by weight; an increased nitrogen content, preferably in a concentration of 0.5% by weight to 17% by weight, particularly preferably in a concentration of 5% by weight to 12% by weight; an increased carbon and nitrogen content, preferably in a concentration of carbon of 0.5% by weight to 7% by weight, particularly preferably in a concentration of 0.5% by weight to 4% by weight, in particular 0.5% by weight to 2% by weight, and of nitrogen, 0.5% by weight to 17% by weight, particularly preferably 5% by weight to 12% by weight; or a decreased carbon content, preferably in a concentration of 0.1% by weight to 0.3% by weight, particularly preferably in a concentration of 0.15% by weight to 0.25% by weight. Such an implant according to the invention also has the advantages described above.

As described above, it is advantageous that such an implant has pores in and/or near the surface. These pores are used in particular for accommodating a pharmaceutically active substance, or for improved anchoring of the implant in the tissue of the treated body.

As stated above, it is also advantageous for the surface of the implant body to have a coating, at least in places, which contains a pharmaceutically active substance.

It is further preferred for the body of the implant to be composed primarily of iron, preferably greater than 80% by weight, particularly preferably greater than 99% by weight iron, in particular in an alloy.

The method according to the invention and the implant according to the invention are explained below with reference to examples and the FIGURE. All of the features shown in the FIGURE and described constitute subject matter of the invention, regardless of their summary in the claims or back-references. For all of the examples described below, as a result of the heat treatment the reduction in the degradation time is at least 75%, in some cases 60%, compared to the degradation time for the particular implant when no heat treatment has been carried out. The degradation time may be further reduced by tribochemical treatment described below.

EXAMPLE 1 (variant I)

A steel such as C10, C15, or C20, for example, was treated by carburization and cooled in such a way that the required mechanical properties ($Rp_{0.2}$ at least 300 MPa and $A_5$ at least 15%) were attained. A carburization depth of approximately 5 μm to 20 μm was set. The total carbon content in the treated implant did not exceed 0.45% by weight.

The parts to be carburized were placed in gaseous atmospheres containing hydrocarbons. In a heat treatment apparatus (carburizing oven) a carburization atmosphere was produced which consisted of a slightly reducing carrier gas and an enrichment gas supplied in a controlled manner. The typical composition of the carrier gas was 20% by volume carbon monoxide, 40% by volume hydrogen, and 40% by volume nitrogen. The enrichment gas was a hydrocarbon, for example methane or propane. The process temperature was between 850° C. and 900° C. For the referenced carburization depths of 20 μm maximum, the maximum treatment time was 10 minutes. The implants were then removed from the oven chamber and cooled in still air.

EXAMPLE 2 (variant I)

Bodies of implants, for example stent bodies, composed of steels C10, C15, or C20 were placed in a gas nitriding oven. Ammonia ($NH_3$) was used as a nitrogen-releasing carrier gas. Due to the filigreed structure of the stent body no liquid or solid nitrogen carriers were used.

During gas nitriding, ammonia ($NH_3$) is continuously split into the components atomic nitrogen and hydrogen over the entire duration of the heat treatment. These processes take place under the influence of heat and the catalytic activity of the iron surface. The nitrogen, which at that point is in atomic form, diffuses into the implant surface. The nitriding temperature during gas nitriding was approximately 500° C. to 530° C. The nitriding time was 10 minutes to 20 minutes. The implants were then removed from the oven chamber is and cooled in still air.

EXAMPLE 3 (variant I)

Steel C15 has the following starting composition (figures are in % by weight): C (0.12-0.18); Si (max. 0.40); Mn (0.30-0.60); P (max. 0.045); and S (max. 0.045).

A stent body made of C15 steel and having the stated composition was nitrocarburized. Nitrocarburization is a combination of carburization and nitriding. For stents it is advantageous to carry out nitrocarburization in the gas phase. If treatment were carried out in relatively high-viscosity molten salts, salt crusts would form between the stent structures and thus prevent inward diffusion of the nitrogen and carbon.

The temperature for the heat treatment during nitrocarburization was in a range between 700° C. and 800° C. The gas atmosphere was comparable to that of Example 1 (variant I), except that ammonia was added. The gas atmosphere was 20% by volume CO, 30% by volume $H_2$, 10% by volume $NH_3$, and 40% by volume $N_2$. The treatment time was approximately 10 minutes in this case as well. The treated stent bodies were then removed from the oven chamber and cooled in still air.

EXAMPLE 4 (variant II)

This example concerns a stent made of a degradable iron-based alloy containing 12% by weight Mn and an initial C content of 0.7% by weight.

Used as starting material was a tube from which a stent was to be manufactured, composed of an iron-based alloy containing 12% by weight Mn and 0.7% by weight C, and having an outer diameter of 2.0 mm and a wall thickness of 120 µm. The composition of the material in the initial state resulted in an austenitic structure. In the tensile test the raw material had a minimum tensile strength $R_m$ of 800 MPa, with a minimum elongation at break $A_5$ of 15%.

A stent for coronary applications was cut from this tube, using laser cutting. After the customary process steps such as deburring, corundum blasting, and electropolishing necessary for edge rounding, the structure of the tube was still austenitic. The stent body thus produced was a tubular strut structure. The cross section of a single strut for the stent body after completion of the referenced steps was approximately 100 µm×100 µm. Annealing (decarburization) in an oxygen atmosphere was then performed at 900° C. to 1000° C. over a period of 30 minutes. In this manner the C content in the near-surface boundary layer was reduced as a function of depth. Cooling was performed by sudden forced ventilation of the oven chamber with nitrogen. This resulted in cooling of the stent to 500° C. within 180 seconds.

The C content resulting from the above heat treatment was still only 0.1% at a depth of 5 µm. The edge decarburization continued to a depth of 40 µm. At this point the C content was 0.6%. In this case the structural state was still austenitic.

The stent was then removed from the heat treatment chamber, crimped, and installed in a catheter.

For clinical use, this stent was dilated to a final diameter of 3.5 mm by use of a balloon. In the zones of the stent undergoing the most intense plastic deformation, a phase change from the austenitic to the martensitic phase occurred in the boundary layer. The transformation zone extended to a depth of 15 µm. At that point the C content was 0.2% by weight. Since the surface decarburization effects occurred over all four sides of the stent structure (former tube interior, former tube exterior, and two laser-cut edges), the original C content was still 0.7% by weight only in a cross sectional width of 20 µm×20 µm. Thus, as a result of the heat treatment the maximum C content of the overall stent was reduced to 0.45% by weight.

EXAMPLE 5 (variant II)

This example concerns an orthopedic endoprosthesis made of a degradable iron-based alloy containing 12% by weight Mn and an initial C content of 0.7% by weight.

This exemplary embodiment corresponds to Example 4; instead of the stent a screw was used for fragment stabilization after expansion of cranial sutures in patients with craniosynostosis. Such an endoprosthesis, for example a cortical screw having a diameter of 1.5 mm and a thread depth of 0.5 mm, was subjected to heat treatment analogous to Example 4. The structural composition resulting from the heat treatment corresponded to that described in Example 4.

No stress corrosion cracking occurs in such an endoprosthesis due to the lack of pulsing mechanical load in the skull region. For this reason, this endoprosthesis degrades somewhat more slowly than the one described in Example 4. However, the screw was still metabolized by the bone of the skull within 12 to 18 months. In this exemplary embodiment the structural transformation occurred exclusively in the region of the screw thread flanks. The surfaces of the thread were crimped upon screwing into the inner thread of a bone plate, likewise composed of a degradable iron alloy, and were thus plastically deformed. This deformation resulted in the described surface structure transformation. The result of the structural transformation is also referred to as "friction martensite."

EXAMPLE 6 (variant I)

This example concerns an endoprosthesis made of a multilayer composite.

First, an Fe tube having a wall thickness of 40 µm and a carbon content of 0.1 to 0.2% by weight and composed of a C15 steel or a C10 steel, the latter containing 0.07% by weight to 0.13% by weight C (the other elements being the same as for the C15 steel described above), was drawn into the matrix. A first heat treatment in a carbon-containing atmosphere was then carried out at approximately 900° C., with a carburization depth of 5 to 20 µm.

A second tube was then drawn in and placed above the previously carburized first tube, thus forming a casing around the first tube. The second tube likewise had a wall thickness of approximately 40 µm, so that the overall wall thickness of the stent body was 80 µm. If three tubes were used, the overall wall thickness of the stent body would accordingly be 120 µm. A second thermochemical treatment was then carried out in a carbon-containing atmosphere at 900° C., resulting in carburization to a depth of 5 to 20 µm. On the one hand the outer surface of the tube was carburized, and on the other hand the carbon diffused, from the boundary layer of the first tube produced by the first carburization step, from the interface into the second tube, thus forming a connecting zone (connecting layer) between the first and the second tubes (or between the second and the third tubes). This connecting zone increases the adhesion between the respective tubes and also minimizes the carbon gradients in the transition between two tubes. The last two process steps may be repeated until the stent has attained the desired wall thickness.

The surface of the stent body may also be tribochemically treated with chloride-containing media after completion of the heat treatments. Such a tribochemical treatment may also be carried out in conjunction with the implants manufactured according to Examples 1 through 5.

The salts used for the tribochemical treatment are composed of a mixture of 50% by weight of NaCl and $MgCl_2$ each. The blast particles have a particle size which varies between 200 nm and 20 μm. By use of compressed air at a pressure of 3 to 4 bar, the blast particles are simultaneously blasted onto the interior and exterior of the implant, using a blasting unit. The process is carried out over a period of 5 minutes. To prevent agglomeration of the hygroscopic salt mixture, the salt mixture must be kept dry before and during the tribochemical treatment process.

Upon striking the surface of the implant, the chloride blast particles are split into numerous small fragments, some of which are reflected from the surface and bounce off same. The fragments of the blast particles which adhere to the surface react with the implant material in the above-described manner and produce submicro-roughnesses. Hard material particles which are optionally used likewise produce micro-roughnesses.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A method for manufacturing a biodegradable implant, wherein the implant is an endovascular stent, the method comprising the following steps:
    a) providing a first part of an endovascular stent body, wherein the body comprises a metallic material, optionally iron; and
    b) performing a heat treatment on the body which alters a content of boron, or decreases a content of carbon in a structure of a near-surface boundary layer in the first part of the body in such a way that strain on a lattice or a lattice transformation, optionally following a subsequent mechanical load, is achieved in the near-surface boundary layer.

2. The method according to claim 1, wherein after step b) a second part of the endovascular stent body is provided, after which the second part is positioned over the first part in such a way that the second part adjoins the first part, at least in a partial region of the near-surface boundary layer, and a system composed of the first and second parts is then subjected to heat treatment according to step b).

3. The method according to claim 1, wherein during the heat treatment according to step b) the boron content in the structure of the near-surface boundary layer is increased by boronization, the boundary layer optionally having a maximum thickness of approximately 300 μm.

4. The method according to claim 3, wherein the average concentration of boron in the near-surface boundary layer after the boronization is approximately 1% by weight to approximately 20% by weight.

5. The method according to claim 1, wherein during the heat treatment according to step b) the content of carbon in the structure of the near-surface boundary layer is reduced by decarburization, the boundary layer optionally having a maximum thickness of approximately 50 μm.

6. The method according to claim 5, wherein the average concentration of carbon in the near-surface boundary layer after the decarburization is approximately 0.1% by weight to approximately 0.3% by weight.

7. The method according to claim 5, wherein if the heat treatment is to decrease the content of carbon the part of the implant body treated by decarburization is quickly cooled.

8. The method according to claim 1, wherein after the heat treatment according to step b), tribochemical treatment of the body is carried out on at least a portion of the surface thereof, and/or coating of the body with a pharmaceutically active substance is carried out on at least a portion of the surface thereof.

9. The method according to claim 1, wherein the body comprises manganese.

10. The method according to claim 1, wherein the treatment configures the endovascular stent to crack at the near surface area upon application of a mechanical load on the endovascular stent to facilitate degradation.

11. The method according to claim 1, wherein the body is dilatable, further wherein the treatment configures the dilatable body to crack at the near surface area upon application of a mechanical load after dilation to facilitate degradation.

12. A method for manufacturing a biodegradable implant, the method comprising the following steps:
    a) providing a first part of an implant body, wherein the body comprises a metallic material, optionally iron; and
    b) performing a heat treatment on the body which alters a content of boron, or decreases a content of carbon, in a structure of a near-surface boundary layer in the first part of the body in such a way that strain on a lattice or a lattice transformation, optionally following a subsequent mechanical load, is achieved in the near-surface boundary layer, wherein during the heat treatment the boron content in the structure of the near surface boundary layer is increased by boronization, the boundary layer optionally having a maximum thickness of approximately 300 μm, further wherein the average concentration of boron in the near-surface boundary layer after the boronization is approximately 1% by weight to approximately 20% by weight.

13. The method according to claim 12, wherein the average concentration of boron in the near-surface boundary layer after the boronization is approximately 7% by weight to approximately 10% by weight.

14. The method according to claim 12, wherein the implant is an endovascular stent.

15. The method according to claim 12, wherein the implant is selected from the group consisting of a bone screw, a bone plate, a bone pin, an intramedullary pin, a spiral bundle nail, a Kirschner wire, a wire for septal occluders, a surgical suture, an intestinal clamp, a vessel clip, and an electrode anchoring element.

16. The method according to claim 12, wherein the treatment configures the implant to crack at the near surface area upon application of a mechanical load on the implant to facilitate degradation.

17. A method for manufacturing a biodegradable implant, wherein the implant is an endovascular stent, the method comprising the following steps:
    a) providing a first part of an endovascular stent body, wherein the body comprises a metallic material, optionally iron; and
    b) performing a heat treatment on the body which alters a content of boron or nitrogen in a structure of a near-surface boundary layer in the first part of the body in such a way that strain on a lattice or a lattice transformation, optionally following a subsequent mechanical load, is achieved in the near-surface boundary layer.

18. The method according to claim 17, wherein the body is dilatable.

19. The method according to claim 17, wherein during the heat treatment according to step b) the nitrogen content in the structure of the near-surface boundary layer is increased by nitriding, or carbon and the nitrogen content in the structure of the near-surface boundary layer is increased by nitrocarburization, the boundary layer optionally having a maximum thickness of approximately 150 μm.

20. The method according to claim 19, wherein the average concentration of nitrogen in the near-surface boundary layer after the nitriding is approximately 0.5% by weight to approximately 17% by weight, optionally approximately 5% by weight to approximately 12% by weight.

21. The method according to claim 17, wherein the treatment configures the body to crack at the near surface area upon application of a mechanical load after dilation to facilitate degradation.

22. The method according to claim 17, wherein during the heat treatment according to step b) the boron content in the structure of the near-surface boundary layer is increased by boronization, further wherein the average concentration of boron in the near-surface boundary layer after the boronization is approximately 1% by weight to approximately 20% by weight.

* * * * *